United States Patent [19]
Arnold

[11] Patent Number: 5,427,613
[45] Date of Patent: Jun. 27, 1995

[54] GLASS IONOMER CEMENT COMPOSITIONS AND RESTORATIVE METHODS

[75] Inventor: Thomas J. Arnold, Winslow, Ind.

[73] Assignee: Mion International Corporation, Winslow, Ind.

[21] Appl. No.: 313,885

[22] Filed: Sep. 28, 1994

Related U.S. Application Data

[60] Division of Ser. No. 79,332, Jun. 18, 1993, Pat. No. 5,382,284, which is a continuation-in-part of Ser. No. 942,375, Sep. 9, 1992, Pat. No. 5,252,122, and a continuation-in-part of Ser. No. 872,501, Apr. 23, 1992, Pat. No. 5,525,121, and a continuation-in-part of Ser. No. 991,112, Dec. 16, 1992, Pat. No. 5,273,574.

[51] Int. Cl.$^6$ .......................... A61K 6/05; A61K 6/06
[52] U.S. Cl. ...................... 106/35; 523/116; 523/118; 433/228.1
[58] Field of Search ................... 106/35; 523/116, 118; 433/228.1

[56] References Cited

PUBLICATIONS

Elliott et al., Physical & Mechanical Properties of Glass–Ionomer Cements, British Polymer Journal, *1975, 7:297–306.
Mitra, Adhesion to Dentin & Physical Properties of a Light–cured Glass Ionomer Liner/Base, Journal of Dental Research 70(1):72–74, Jan. 1991.
Nathanson et al., The Significance of Retention in Post and Core Restorations, PP&A, The AACD Symposium Edition, vol. 5, No. 3, 82–89, Apr. 1993.
Browne et al., Soluble Aluminum Silicates: Stoichiometry, Stability and Implications of Environmental Geochemistry, Science, vol. 256:1667–1670, 19 Jun. 1992.
Wasson et al., New Aspects of the Setting of Glass–Ionomer Cements, Journal of Dental Research 72(2):481–483, Feb. 1993.
Swift, Jr., A review of dentin bonding, General Dentistry, Sep.–Oct. 1988:396–399.
International Publ. No. WO92/11837, Adhesive Amalgam System, Published 23 Jul. 1992.

*Primary Examiner*—Paul Lieberman
*Assistant Examiner*—Margaret Einsmann
*Attorney, Agent, or Firm*—Ice Miller Donadio & Ryan; Paul B. Overhauser; Doreen J. Gridley

[57] ABSTRACT

A restoration for restoring a lesion in a tooth and method for making the same. The restoration comprises a layer of glass ionomer cement bonded to the lesion and a layer of amalgam disposed on the layer of glass ionomer cement. The restoration is formed by the process of applying a layer of wet glass ionomer cement on the lesion, placing a wet dental amalgam directly on the wet glass ionomer cement, and allowing the wet glass ionomer cement and the wet amalgam to harden to bond the amalgam to the tooth. Various modifications to the glass ionomer cement are disclosed to either improve the bond of the restoration's amalgam to the tooth or to enhance the cement's use in various dental procedures. Also disclosed are various dental procedures using the restoration and method of making the restoration which results in the resolution of certain shortcomings of current like procedures.

5 Claims, No Drawings

GLASS IONOMER CEMENT COMPOSITIONS AND RESTORATIVE METHODS

CROSS REFERENCE TO RELATED APPLICATIONS

This is a divisional application of application Ser. No. 08/079,332, filed Jun. 18, 1993 now U.S. Pat. No. 5,382,286, which is a continuation-in-part of application Ser. Nos. 07/942,375, filed Sep. 9, 1992, now U.S. Pat. No. 5,252,122; 07/872,501, filed Apr. 23, 1992, now U.S. Pat. No. 5,525,121; and 07/991,112, filed Dec. 16, 1992, now U.S. Pat. No. 5,273,574.

FIELD OF THE INVENTION

This invention relates to dental restorations, and, in particular, to dental restorations using glass ionomer cement and amalgam.

BACKGROUND OF THE INVENTION

Since its introduction to the United States in the late 1970's, glass ionomer cements have gained a great deal of popularity for use in various dental procedures. The interest in using glass ionomer cements for a myriad of purposes stems from the cement's ability to bond to both dentin and enamel, the fact that the cement is tooth-colored when hardened, and because glass ionomer cements generally contain fluorides which are thought to minimize the occurrence of decay to the tooth surface to which the glass ionomer cement is applied. Initially, glass ionomer cements were generally used for restorations. These glass ionomer cements, known as Type II glass ionomer cements, are of a larger particulate matter than are the Type I glass ionomer cements used for other purposes. When these Type II glass ionomer cements are used as a restoration material, the lesion in a tooth is prepared by standard techniques as may be performed for cavity preparation for the placement of an amalgam restoration thereon; however, it may not be necessary to create an undercut for a glass ionomer restoration. Care must be taken to make certain that the preparation is free of moisture as glass ionomer cement in such an application is extremely susceptible to water contamination and dehydration during the initial setting stage.

Type I glass ionomer cements are typically used as a base, liner, or luting agent. When used for these purposes, the surface of the tooth again must be substantially free from moisture during application as well as throughout the hardening process of the glass ionomer cement. In addition to its use as restorations, base, liner or luting agent, glass ionomer cements are also used for affixing restorations to a tooth. For composite restorations, such as ceramic or porcelain prostheses, the glass ionomer cement is allowed to harden and then is etched before placement of the composite restoration thereon. For those restorations containing metal, the glass ionomer cement need not be hardened first as wet glass ionomer cement is known to adhere to cast metals.

Glass ionomer cements are generally comprised of a powder component containing aluminosilicate and a liquid portion. Often the liquid portion is expressed as containing polyacrylic acid, polymaleic acid, polyitaconic acid, or a copolymer of at least two of the acids. The liquid portion may also comprise carboxylate polymers or carboxylic acid polymeric structures, such as those including acrylic acid, maleic acid, crotonic acid, isocrotonic acid, methacrylic acid, sorbic acid, cinnamic acid, fumaric acids and the like. "New Aspects of the Setting of Glass-ionomer Cements," Wasson et al., *Journal of Dental Research*; Vol. 72, No. 2, February, 1993; pages 481–483. In all glass ionomer cements, the primary reactions which cause the glass ionomer cement to harden is cross-linking, i.e., the cross-linking of polycarboxylate chains by metal ions from the glass. Also, during setting, the acids of the glass ionomer cement dissolve the glass structure to release metal constituents of the glass. Metal carboxylates are formed during the setting process. This may be distinguished from the primary setting reactions of acrylic cements which are other forms of polymerization reactions. Though other forms of polymerization reactions may occur in glass ionomer cements, these reactions are secondary to the cross-linking reactions of the glass ionomer cement.

Recently, it was discovered that wet glass ionomer cement bonds well with wet amalgam. As disclosed in U.S. patent application Ser. No. 07/942,375, filed Sep. 9, 1992, now U.S. Pat. No. 5,252,122 a dental restoration is formed by applying a layer of wet glass ionomer cement to a lesion in a tooth, placing a layer of wet amalgam directly on the layer of wet glass ionomer cement, and allowing the cement and the amalgam to harden to thereby bond the amalgam to the tooth. Such a restoration is beneficial in that the cavity preparation need not be undercut for the placement of an amalgam restoration. Further, the glass ionomer cement does not appear to be as moisture sensitive in such a procedure. Finally, the creation of the restoration is less time consuming than is a restoration in which the glass ionomer cement is hardened and then etched before the lesion is filled with amalgam.

Because glass ionomer cements have so many appealing qualities to the dental profession, numerous variations of glass ionomer cements have been developed to enhance particular properties of the glass ionomer cements for specific applications. For example, U.S. Pat. No. 4,738,722, discloses a glass ionomer cement containing additives such as zinc oxide and titanium oxide. These additives improve the glass ionomer cement by eliminating pulpal sensitivity and also affect the setting time of the cement. Specifically, reducing the setting time of the cement with the introduction of these additives is beneficial when the glass ionomer cement is used as a base, liner, or luting agent wherein it is desirable to have a quick setting cement for the completion of further procedures thereafter.

In U.S. Pat. No. 4,064,629, large metal particles are added to a glass ionomer cement. In this manner when the cement is used as a base or liner for an amalgam restoration, application of a wet amalgam to a hardened glass ionomer cement essentially results in the cross-amalgamation of the mercury in the amalgam with the large metal particles in the cement. This additive assists in strengthening the bond between the hardened glass ionomer cement base and the amalgam restoration.

Another approach to strengthening the glass ionomer cement without effecting its adhesive properties is disclosed in U.S. Pat. No. 4,738,722. Specifically, manufacturers have been known to add the powder component of an amalgam to the glass ionomer cement. Such an additive may be particularly helpful when using a glass ionomer cement as a restoration. Yet another additive is disclosed in Japanese Patent No. 2,275,731. In this patent, zinc oxide and zirconium oxide are added to the glass ionomer cement to improve its resistance to disintegration and crushing and to improve its hardening time.

Another problem associated with glass ionomer cement is its tendency to shrink as it dries in relation to a reduction in the environmental humidity. In response to this problem, an additive mixture to glass ionomer cement comprising quartz sand, cristobalite flour and zirconium silicate was added in a study discussed in the article "Physical and Mechanical Properties of Glass-Ionomer Cements", Elliott, et al., *British Polymer Journal*, 1975, 9, 297–306. Though the additive mixture assists in reducing shrinkage in a less humid environment, it was also found to reduce the compressive strength of the cement.

Disclosed in U.S. patent application Ser. No. 07/991,112, filed Dec. 16, 1992, now U.S. Pat. No. 5,273,574 is an additive comprising zircon for use with the wet glass ionomer cement to wet amalgam restorative method of U.S. patent application Ser. No. 07/942,375, now U.S. Pat. No. 5,252,122. The zircon additive, in this application of glass ionomer cement, is thought not to interfere with any of the normal chemical reactions of the glass ionomer cement while allowing the practitioner to adjust the color, handling characteristics, and the setting time of the cement.

In addition to modifying the glass ionomer cement, improvements have been made with regard to the wet glass ionomer cement to wet amalgam bond by mixing an additive to the amalgam. Specifically, in U.S. patent application Ser. No. 07/872,501, filed Apr. 23, 1992, now U.S. Pat. No. 5,252,121, additives from the group of metal salts, metal bases and metal oxides are added to the amalgam to improve such a bond. Such an additive may comprise, for example, the powder component of a polycarboxylate cement.

With each of the various dental procedures for which glass ionomer cements are known to be used, it is desired to improve upon certain characteristics of this cement depending on the particular use of the cement. As previously noted, a relatively quick setting time is desired when the glass ionomer cement is being used as a base, liner or luting agent or when used to affix a composite restoration to a tooth. This desire is based on the requirement for the glass ionomer cement to first harden prior to the completion of subsequent dental procedures. Further, any improvements which can be made for any use of a glass ionomer cement which inhibits secondary caries or which strengthens the glass ionomer cement are generally desirable.

In addition to serving as a restoration, amalgam has been used for a variety of dental procedures. For example, there are instances in which it is desirable to build an amalgam post or an amalgam core for attachment of a prosthesis to the tooth. A post is defined as a solid structure which extends into a hole in the tooth, generally a hole formed in the root canal of the tooth. A core extends above the root tooth surface and is generally of larger mass than is a post. Should amalgam be used to build a post or a core, generally, the tooth surface must be undercut to mechanically retain the amalgam within the undercut tooth structure after the amalgam has hardened. Such undercutting is not feasible in all instances depending on the tooth structure remaining and from which the post or core is to extend. Thus, the use of amalgam posts and/or cores may not always be feasible even though desirable for their known strength and adaptability or formability within the tooth. Therefore, it is desired to develop a method for building an amalgam post and/or an amalgam core which does not require undercutting of the remaining tooth structure.

When an amalgam core is used for the application of a prosthesis thereon, difficulty for the dentist and the patient arises in the amount of time usually required for the completion of such a procedure. First, in many instances this involves a multi-step process whereby the core is cemented to the tooth, or, alternately, may involve the application of an amalgam core as previously discussed. In either instance, the core or cement must be allowed to harden. Then, before the prosthesis may be applied to the core with a cement, the core must be properly shaped for the prosthesis or the prosthesis must be made to fit the shape of the core. Again, a period of time expires in treatment. Now, the cement can be used to affix the prosthesis to the core to harden. It is therefore desirable to develop a method for applying both a core and a prosthesis thereon which consumes less time than is currently required.

Another dental procedure to which improvements may be made is that of post cementation. Generally, a hole is prepared in the canal of the tooth for receipt of a post. The cement is spinned or applied into the hole and the post is coated with a cement. The post is then placed into the hole and the cement is allowed to harden such that the cement holds the post's place within the hole. For stainless steel and titanium posts, a variety of cements may be used for this purpose; however, for these posts, cements are known to be deficient to adequately provide the desired rigidity and strength. Therefore, it is desired to provide a method of post cementation that may be utilized with a post of any material to increase the stability with which the post is retained within the hole.

The application of sealants to teeth often poses problems desired to be overcome. In many instances, sealants are applied to a child's teeth with the intent of protecting the tooth. Regardless of the age of the patient, the sealant, usually an acrylic, is applied after etching, rinsing and drying the tooth. The sealant is then allowed to harden. This procedure may take upwards of three minutes to complete. During this period, it is very difficult to isolate moisture from the area to be sealed. Such moisture may reduce the bond between the sealant and the tooth. Therefore, it is desired to develop a procedure for sealing teeth which is less time consuming than the described procedure. In addition, it is desired to provide a sealant which may be used without etching the tooth surface to be sealed. Also, the life expectancy of acrylic sealants is typically five years. There are instances when this period of time is not sufficient and it is therefore desired to develop a sealant having a longer life span. Finally, acrylic sealants do not chemically inhibit the development of secondary caries. Therefore, it is desired to inhibit such decay with the use of a sealant containing fluorides or like decay-inhibiting materials.

There are some instances in which it is desired to splint two teeth together. Such a procedure may be necessary, for example, should a tooth be jarred loose as may be caused by an accident. Generally, the procedure for splinting teeth together today involves cementing the adjacent teeth together by applying crowns thereon. Such a procedure is therefore costly. It is desired, then, to reduce the cost of splinting teeth together as may be necessary to resolve a temporary problem or when the patient is unable to afford a more expensive procedure.

In summary, glass ionomer cements have been used for a variety of purposes since their introduction. Variations on the chemical composition of the glass ionomer cements have proved helpful in the use of glass ionomer cements for particular dental procedures and yet further improvements are desired. In addition, there are numerous dental procedures for which cementing techniques may be utilized and which as currently performed may exhibit difficulties, inconveniences or problems which are desirable to be addressed in the development of new or improved methods.

OBJECTS OF THE INVENTION

Accordingly, it is one object of the present invention to provide an additive for glass ionomer cement which improves the strength of the cement without altering its chemical reactions.

It is another object of the present invention to provide a method for building an amalgam core or an amalgam post which does not require that the remaining tooth structure be undercut.

It is still another object of the present invention to provide a method for building a core and attaching a prosthesis thereto that is less time consuming to perform than is required with current procedures.

It is another object of the present invention to provide a post cementation method that may be used to cement any post (including those made of stainless steel or titanium) and which results in an increase in the retentive forces.

It is still another object of the present invention to provide a dental sealant which is less time consuming to apply than are acrylic sealants, is capable of being used to seal adjoining grooves in the tooth surface to be sealed without etching the tooth, has an increased life expectancy over acrylic sealants and inhibits the development of decay.

It is yet another object of the present invention to provide a method for splinting adjacent teeth together which is less expensive than the application of a crown over the teeth.

SUMMARY OF THE INVENTION

A restoration for restoring a lesion in a tooth comprises a layer of glass ionomer cement bonded to the lesion and a layer of amalgam disposed on the layer of glass ionomer cement. The restoration is formed by the process of applying a layer of wet glass ionomer cement on the lesion, placing a wet amalgam directly the layer of wet glass ionomer cement, and allowing the cement and the amalgam to harden to thereby bond the amalgam to the tooth. This process is also referred to herein as the wet-to-wet process or method.

In one embodiment, the glass ionomer cement of the restoration includes diamond microcrystals which increase the compressive strength of the cement and which provides a mechanism whereby the contraction of the cement during hardening can be controlled. By controlling the contraction of the cement, the expansion of the amalgam occurring during its hardening may be accommodated.

In another embodiment, the glass ionomer cement comprises an antibiotic compound to assist in reducing the possibility of secondary caries from the restoration. In yet another embodiment, the glass ionomer cement contains at least one additive from the group of metals, metal salts and metal oxides to improve the bond strength of the restoration. Wet dental amalgam is mixed throughout the cement in another embodiment of the glass ionomer cement to further enhance the bond strength and to improve upon the cement's compressive strength.

Various methods are presented herein in which the restoration created by the wet-to-wet process is used to resolve shortcomings of present dental procedures. An amalgam post or amalgam core is formed by the wet-to-wet process, thereby eliminating the need to undercut the tooth surface for retention of the amalgam. For cementing posts within a canal hole in a tooth, the wet-to-wet process is utilized to assist in retaining the post within the canal hole. This post-cementation method may be used for posts made of materials such as titanium which are presently difficult to cement to a tooth. Also, the wet-to-wet method is used in affixing a prosthesis to an amalgam core extending from the tooth which reduces the amount of time necessary to complete such a procedure. The wet-to-wet method is also used to quickly and easily seal a tooth or teeth as well as adjoining grooves in the tooth with such a sealant having an improved life expectancy and resistance to decay when compared to acrylic sealants. In addition, the wet-to-wet method is used to splint adjacent teeth together at a cost that is significantly less than the application of a crown to the adjacent teeth.

DETAILED DESCRIPTION

U.S. patent application Ser. No. 07/942,375, filed Sep. 9, 1992, now U.S. Pat. No. 5,252,122 incorporated herein by reference, discloses a method for restoring a lesion in a tooth as well as a restoration formed by that method. Specifically, the method involves the steps of applying wet glass ionomer cement to a lesion, placing wet dental amalgam directly on the wet glass ionomer cement, and allowing the wet glass ionomer cement and the wet dental amalgam to harden. In this manner, the amalgam is bonded to the tooth. The restoration formed by this method comprises a layer of glass ionomer cement bonded to the tooth and a layer of amalgam disposed on the layer of glass ionomer cement. The method and restoration are advantageous in that no retentive pins or acid etching is required for bonding an amalgam restoration to the tooth. Also, a large lesion or cavity may be filled by such restoration without requiring that the tooth be undercut for the retention of such a restoration. Though disclosed as applicable to a lesion, the method may utilized on any tooth surface. For example, a portion of the tooth may be broken off and the method used to restore the tooth to its desired form. The method may also be used to form an amalgam veneer on any tooth surface and may even be applied to a substantially vertical surface.

As previously mentioned herein, glass ionomer cements contain metal carboxylates formed during the setting process of the cement. The primary reaction causing the glass ionomer cement to harden is the cross-linking of polycarboxylate chains by metal ions from the glass. Thus, a glass ionomer cement when wet is a carboxylate-containing cement. As used herein, and in the claims, the term glass ionomer cement encompasses cements or adhesives using this primary reaction of cross-linking. Further, because the presence of metal carboxylates is critical to the formation of the ionic bond of the amalgam to the tooth in the method of U.S. patent application Ser. No. 07/942,375, now U.S. Pat. No. 5,252,122 (the "wet-to-wet" method), the cement must necessarily be carboxylate-containing. It is possible for a carboxylate-containing cement or adhesive to be comprised of cements other than a pure glass ionomer cement to achieve the desired bond. In addition to cements comprising a glass ionomer cement and an additive or additives thereto, the cement may comprise a mixture of different types of cements and still be contemplated as within the scope of the invention. For example, a mixture of glass ionomer cement and an acrylic cement contains carboxylates and therefore may be utilized in the wet-to-wet method.

It will be appreciated by those of skill in the art that the wet-to-wet method does not require that the tooth to be restored first be etched nor does a primer need to be applied. This results in an expedient procedure for restoring a tooth. However, it is possible that an etchant or primer is first applied to the tooth prior to the application of the glass ionomer cement. Though the application of an etchant and/or primer increases the time necessary to create the restoration, it may be desirable should its presence increase the bond of the amalgam to the tooth or should the dentist's preferences dictate the use of an etchant or primer.

Considering first the use of a primer, primers, sometimes referred to as dentin pretreatment materials, are used with acrylic bonding systems as well as in other dental restorative procedures. In acrylic bonding systems, the tooth is first etched and then a primer is applied to the tooth and allowed to harden. An acrylic bonding agent is then disposed on the primer and then the amalgam is applied to the bonding agent. Examples of primers used with bonding agents include hydroxyethyl methacrylate (HEMA), HEMA and glutaraldehyde, ferric acid, and phosphonated dimethacrylate combined with ethanol, water and comphoroquinone. Though some primers may reduce the bond strength of the ionic bond of the amalgam to the tooth in the wet-to-wet method, other, such as ferric chloride, may present ions which enhance the ionic bond of the amalgam to the tooth.

Though glass ionomer cements bond well to dentin, a dentist may desire to prepare the tooth surface with an etchant with the intent of enhancing the bond of the restoration to the tooth. Examples of etchants used today in dentin bonding systems as well as in other restorative procedures include ether-acetone, hydrogen peroxide and alcohol, citric acid, phosphoric acid and ethylenediaminetetraacetic. Application of an etchant to the tooth prior to the application of the glass ionomer cement is contemplated to be within the scope of the invention as the glass ionomer cement is still applied directly to the tooth and an ionic bond between the amalgam and the tooth results from the application of wet amalgam on the wet glass ionomer cement.

In terms of improvements to the glass ionomer cement as may be used in the restoration and method (the "wet-to-wet" method) of U.S. patent application Ser. No. 07/942,375, now U.S. Pat. No. 5,252,122, it is desirable for the glass ionomer cement to accommodate the known expansion of amalgam during the amalgam's hardening process. The expansion of amalgam is generally advantageous in that it assists in sealing the amalgam restoration to the tooth. It is therefore preferable that the glass ionomer cement not hinder the early setting expansion of the amalgam for this reason. By creating a glass ionomer cement which controls the contraction while hardening at an amount substantially equivalent to the dimensional changes of wet amalgam in early amalgamation, the restorative bonding stress between the layer of hardened glass ionomer cement and the layer of hardened amalgam are minimized. In this manner, few gaps between the layers result to thereby improve the bond of the glass ionomer cement to the amalgam as well as the bond of the amalgam to the tooth.

Glass ionomer cements containing inert additives, i.e., those additives which do not appear to interact with the chemical reactions of the glass ionomer cement, have been found to assist in minimizing the restorative bonding stress between the layer of hardened glass ionomer cement and the layer of hardened amalgam. Zircon (zirconia silicate) disclosed as an additive to glass ionomer cement for the "wet-to-wet" method in U.S. patent application Ser. No. 07/991,112, filed Dec. 16, 1992, now U.S. Pat. No. 5,273,574 constitutes such an inert additive. Another inert additive is diamond. According to the present invention, diamond microcrystals are added to the glass ionomer cement for the purpose of reducing the restorative bonding stress between the layer of glass ionomer cement and the layer of amalgam, as well as for improving the overall strength of the glass ionomer cement. This "strength" refers to the cement's compressive strength and its resistance to crushing and disintegration. A glass ionomer cement comprising diamond microcrystals may be formed by adding diamond microcrystals to either the powder component or the liquid component of the glass ionomer cement prior to mixing the powder and liquid together to form a wet cement. To result in a glass ionomer cement having acceptable handling characteristics for a variety of restorative purposes, diamond microcrystals comprise from about 0.1% by weight to about 50% by weight of the total weight of the cement. If, for example, the cement is to be utilized as a restorative material for filling a cavity, a greater percentage of diamond microcrystals is desirable. On the other hand, for use as a base, liner, or luting agent, a lower percentage of diamond microcrystals may be preferable. It is worthy to note that the thickness of the resulting cement decreases with the addition of diamond microcrystals. The additive's affect on viscosity must also be taken into consideration when determining the appropriate amount for use in a particular dental procedure.

It will be appreciated by those of skill in the art that the diamond microcrystals not only increase the strength of the glass ionomer cement, but the diamond microcrystals do so without interacting with the chemical reactions of the glass ionomer cement during hardening. Thus, diamond microcrystals are desirable for a variety of uses of glass ionomer cements including the "wet-to-wet" method of restoring a lesion in a tooth disclosed in U.S. patent application Ser. No. 07/942,375, now U.S. Pat. No. 5,252,122. Also, the diamond microcrystals may be added to glass ionomer cements used for other procedures well known in the art. For example, glass ionomer cement containing diamond microcrystals may be used as a base, as a liner, as a luting agent or as a restorative material.

Because glass ionomer cements are carboxylate-containing adhesives/cements, and because the primary reaction occurring during the setting of the glass ionomer cement is the cross-linking of polycarboxylate chains by metal ions from the glass, improvements to the glass ionomer cement may also be made by adding to the cement an additive or additives in the form of a metal base, metal salt and/or metal oxide. The presence of these metal additives further facilitate the cross-linking of polycarboxylates with the metal ions of glass ionomer cement. Such an additive may comprise from about 2% to about 50% by weight of the total weight of the cement and may be added to either the liquid or powder components of the glass ionomer cement. The metal, metal salt, and/or metal oxide additive(s) may be a combination thereof and assists in increasing the bond strength of wet glass ionomer cement to wet amalgam.

One concern in creating an amalgam restoration is the potential for the development of secondary caries. If decay develops between the tooth and the amalgam restoration, replacement of the amalgam restoration may eventually be required. When replacing an amalgam restoration due to the presence of decay, the decay must necessarily be removed, usually resulting in further loss of enamel and/or dentin. In one embodiment of the present invention, an antibiotic compound is added to the glass ionomer cement with the intent of reducing the development of such secondary caries as well as any residual primary caries. The antibiotic compound may be added to either the powder or liquid components of the cement prior to mixing or may be added to the mixed cement prior to the application of the cement. Antibiotic compounds include chlorhexidine, tetramycin, penicillin, keflex, ampicillin, cephalosporin, and other antimicrobial or antibiotic agents. The antibiotic additive may be added in an amount comprising from about 0.1% by weight to about 35% by weight of the total weight of the glass ionomer cement. When used in conjunction with the "wet-to-wet" restorative method of U.S. patent application Ser. No. 07/942,375 now U.S. Pat. No. 5,252,122, the glass ionomer cement containing an antibiotic compound not only assists in bonding the amalgam to the tooth, but provides an antimicrobial additive to resist the development of secondary caries between the amalgam and the tooth.

In another embodiment of the present invention, just triturated dental amalgam is mixed throughout the glass ionomer cement. "Just triturated" is intended to mean wet dental amalgam wherein the amalgam powder and mercury components of the amalgam have been mixed and the mixture has not yet amalgamated or hardened. By adding wet amalgam to the glass ionomer cement in amounts from about 20% by weight to about 70% by weight of the total weight of the composition, a strong restorative material results. Essentially, the wet-to-wet restorative method is utilized within this restoration as the wet amalgam resides within the wet glass ionomer cement. Such a composition has been found not to affect the amalgamation process and the amalgam continues to amalgamate within the glass ionomer cement, i.e. the amalgam within the glass ionomer cement hardens in concert with the hardening of the glass ionomer cement. For such a restorative material, the glass ionomer cement may be of a composition which accommodates the expansion of the amalgam within the glass ionomer cement such that a restoration using this composition does not place undue stress on the lesion or cavity in which the restoration is applied.

It will be appreciated by those of skill in the art that restorative material comprising wet (just triturated) amalgam in wet glass ionomer cement may be used for dental procedures ordinarily requiring the use of glass ionomer cement alone. In addition to using the restorative material as a restoration, it may be used as a base, liner, core material, or luting agent. The restorative material may also be used with the wet-to-wet restorative method of the present invention.

As previously mentioned herein, there are numerous dental procedures to which improvements may be made. As disclosed herein, the wet-to-wet restorative method of the present invention may be used to improve upon various dental procedures. In one embodiment of the present invention, to create an amalgam post which is to extend from a canal hole in a tooth, glass ionomer cement is used to bond the amalgam post to the tooth according to the wet-to-wet method. Specifically, by applying the wet glass ionomer cement to the hole, packing the wet amalgam into the hole and allowing the amalgam and cement to harden, an amalgam post is formed. The resulting amalgam post may be used in concert with conventional dental procedures requiring a post. It will be appreciated by those of skill in the art that this amalgam post may extend directly above the tooth surface without requiring the tooth surface be undercut as is necessary when amalgam is applied without the use of the wet-to-wet restorative method.

Similar to building an amalgam post, an amalgam core for a tooth may be formed using the wet-to-wet method. By applying a layer of wet glass ionomer cement to the tooth, and then applying a layer of wet amalgam to the layer of wet glass ionomer cement such that the wet amalgam extends above the root portion of the tooth, an amalgam core is formed upon the hardening of the glass ionomer cement and the amalgam. As with the building of amalgam posts, no undercutting is required for building an amalgam core according to the present invention. Of course, the amalgam core according to the present invention may be used in conjunction with a support member, such as a pin or post which extends above the tooth surface. By applying the amalgam intended to form the core about a support member, the support member is utilized to assist in holding the amalgam core in place. It will be further appreciated that use of a support member may be desired when restoring a large lesion or cavity using the wet-to-wet method.

In another embodiment of the present invention, amalgam is used to assist the cementation of a post into a tooth. Specifically, for a tooth having a canal hole therein, a post having a length greater than the depth of the hole is placed into the hole after wet cement is applied to either the hole or the post or both. For example, the cement may be spinned or applied into the hole and/or applied to the portion of the post to be inserted into the canal hole. Use of the cement holds the post in place in the hole. A portion of the post extends above the tooth when placed in the hole. By placing cement about the post at the point at which the post extends above the hole and bonding a wet amalgam to the cement placed above the hole, and allowing the amalgam to harden, the amalgam and cement above the hole assist in retaining the post within the hole. Various amalgam bonding agents may be employed as the cement above the hole in this post cementation method, or tooth structure above the hole may be undercut for retention of the amalgam about the post and above the hole. The wet-to-wet method is also contemplated for use in this post cementation method as well. Specifically, a glass ionomer cement is used and the amalgam is applied to the glass ionomer cement above the hole before the cement hardens. This results in the bonding of the wet amalgam to the wet glass ionomer cement. It will be appreciated by those of skill in the art that cement may extrude from the hole after placing the post into the canal hole. If such an extruded cement results, it is not necessary to apply additional cement above the post as the extruded cement may be used for the bonding purpose.

It will be appreciated that the amalgam applied above the canal hole may also be bonded to the post itself. The post cementation method may be particularly helpful when using an inert metal post (e.g. titanium or gold) as cements generally do not adhere as well to inert metal posts, even though amalgam bonds well with such posts. Though the use of inert metal posts is desirable due to the material's strength, it has been hindered due to the inability to secure these posts within the hole. By using the post cementation method described herein wherein the amalgam contacts the post above the hole, the post is securely cemented within the hole by being bonded to the amalgam which is in turn bonded to the tooth. It will be appreciated by those of skill in the art that regardless of the composition of the post, the placement of this amalgam cap at the top of the hole about the post further assists in retaining the post within the hole. This is true whether or not the amalgam actually contacts and is bonded to the post itself.

The wet-to-wet restorative method of the present invention may also be used to adhere an amalgam core to the tooth for the placement of a prosthesis thereto. By placing wet glass ionomer cement on a lesion in the tooth, packing the wet amalgam into the lesion such that the wet amalgam contacts the wet glass ionomer cement, an amalgam core is formed as previously described herein. A prosthesis may be cemented to the amalgam core with wet glass ionomer cement to form an amalgam core. Such a prosthesis may be, for example, a crown or a bridge. It is also contemplated to be within the scope of the invention to cement the prosthesis over an amalgam core before the amalgam hardens. This significantly reduces the amount of time required for the procedure of building a core and placing a prosthesis thereon as is done in the prior art. Specifically, the amalgam core may be applied directly over the glass ionomer cement without waiting for the cement to harden. Also, the prosthesis may be applied to the amalgam core before the amalgam hardens. It will also be appreciated that a support member, such as a pin or a post, may be used in conjunction with the method of affixing a prosthesis to a core as discussed herein. Such a support member will further assist in retaining the core and prosthesis in position.

To address problems associated with the use of acrylic sealants, the wet-to-wet restorative method of the present invention may be utilized. Specifically, by applying a layer of wet glass ionomer cement on the surface of the tooth to be sealed, placing a layer of wet amalgam directly on the wet glass ionomer cement thereby enabling the glass ionomer cement to bond the amalgam to the tooth, and allowing the glass ionomer cement and the wet amalgam to harden, the amalgam is bonded to the tooth to form a seal. This method results in several advantages over the application of acrylic sealants. First, the sealing method of the present invention is less time consuming than the method using acrylic sealants. Also, the glass ionomer/amalgam sealant is capable of sealing adjoining grooves in the tooth surface to be sealed without etching the tooth. Because the sealing method of the present invention may last a lifetime, it results in a seal having an increased life expectancy over acrylic sealants which typically only last for five (5) years. The glass ionomer/amalgam sealant also inhibits the development of decay. This inhibition of decay results from the fact that glass ionomer cements generally comprise fluoride ions which resist the development of secondary caries.

In yet another embodiment of the present invention, the wet-to-wet method may be used to splint two adjacent teeth together. The splinting method utilizes the wet-to-wet restorative method. First, wet glass ionomer cement is applied to adjacent surfaces of the teeth. Then, a layer of wet amalgam is placed onto the wet glass ionomer cement, and the cement and amalgam are allowed to harden. In this manner, the adjacent teeth are bonded to each other upon hardening of the cement and amalgam. A fastener, such as a stainless steel wire, may be used with the splinting method of the present invention to assist in splinting the adjacent teeth together. By drilling a hole in each of the teeth and cementing the ends of the fastener to the drilled holes prior to the application of the wet glass ionomer cement, the glass ionomer cement and amalgam is then applied about the fastener. This results in the fastener joining the adjacent teeth together in addition to teeth being bonded together by the application of the glass ionomer cement and amalgam according to the wet-to-wet method of the present invention.

It will be appreciated by those of skill in the art that the splinting method of the present invention is less costly than is the conventional solution of placing crowns over the adjacent teeth. Further, the splinting procedure is easily performed in a short amount of time and therefore offers a more viable solution for a temporary problem to be resolved by splinting adjacent teeth together.

What is claimed is:

1. A glass ionomer cement, comprising:
    a powder component comprising aluminosilicate and a liquid component comprising an unsaturated carboxylate containing monomer or polymer or both; and diamond microcrystals.

2. The cement of claim 1 wherein the diamond microcrystals comprises from about 0.1% by weight to about 50% by weight of the total weight of the cement.

3. The cement of claim 1 wherein the diamond microcrystals are included with either the powder component or the liquid component.

4. A restoration for restoring a tooth, comprising:
    a layer of glass ionomer cement bonded to the tooth, the glass ionomer cement comprising
    a powder component and a liquid component as defined in claim 1, and diamond microcrystals; and
    a layer of amalgam disposed on the layer of the glass ionomer cement,
    the restoration being formed by the process of applying a layer of wet glass ionomer cement to the tooth, placing a layer of wet amalgam onto the layer of the wet glass ionomer cement, and allowing the glass ionomer cement and the amalgam to harden.

5. The restoration of claim 4 wherein the diamond microcrystals comprise from about 0.1% by weight to about 50% by weight of the total weight of the cement.

* * * * *